(12) United States Patent
Tani et al.

(10) Patent No.: US 9,120,956 B2
(45) Date of Patent: Sep. 1, 2015

(54) WATER-BASED PLASTER

(75) Inventors: Kazuha Tani, Higashikagawa (JP); Takashi Kamakura, Higashikagawa (JP)

(73) Assignee: Teikoku Seiyaku Co., Ltd., Higashikagawa-shi (JP)

(*) Notice: Subject to any disclaimer, the term of this patent is extended or adjusted under 35 U.S.C. 154(b) by 0 days.

(21) Appl. No.: 14/233,681

(22) PCT Filed: Jul. 18, 2012

(86) PCT No.: PCT/JP2012/068189
§ 371 (c)(1),
(2), (4) Date: Jan. 17, 2014

(87) PCT Pub. No.: WO2013/012000
PCT Pub. Date: Jan. 24, 2013

(65) Prior Publication Data
US 2014/0171555 A1    Jun. 19, 2014

(30) Foreign Application Priority Data

Jul. 21, 2011 (JP) .................... 2011-159912

(51) Int. Cl.
*C09J 133/02* (2006.01)
*A61K 9/70* (2006.01)

(52) U.S. Cl.
CPC ............. *C09J 133/02* (2013.01); *A61K 9/7061* (2013.01)

(58) Field of Classification Search
CPC .............................. C09J 133/02; A61K 9/7061
USPC .................................................. 524/35, 322
See application file for complete search history.

(56) References Cited

U.S. PATENT DOCUMENTS 7,056,528 B1 * 6/2006 Bracht ........................ 424/449

FOREIGN PATENT DOCUMENTS

| JP | 60-226808 A | 11/1985 |
|----|----|----|
| JP | 60-260512 A | 12/1985 |
| JP | 60-260513 A | 12/1985 |
| JP | 60260512 A * | 12/1985 |
| JP | 60260513 A * | 12/1985 |
| JP | 62-63512 A | 3/1987 |
| JP | 6-219940 A | 8/1994 |
| JP | 06219940 A * | 8/1994 |
| JP | 7-89853 A | 4/1995 |
| JP | 07089853 A * | 4/1995 |
| JP | 2001-122771 A | 5/2001 |
| JP | 2003-528037 A | 9/2003 |
| JP | 2006-1860 A | 1/2006 |
| JP | 2006001860 A * | 1/2006 |

OTHER PUBLICATIONS

Kawai "Utilization of isostearic acid and derivatives in cosmetics", Yushi, 1998, vol. 51, No. 8, pp. 46-49.*
International Search Report date Aug. 28, 2012 with English translation (five (5) pages).
Japanese-language International Preliminary Report on Patentability (PCT/IB/373) including Written Opinion (PCT/ISA/237) dated Jan. 21, 2014 with English translation (nine (9) pages).
Kawai, "Utilization of isostearic acid and derivatives in cosmetics," Yushi, 1998, vol. 51, No. 8 (five (5) pages).

* cited by examiner

*Primary Examiner* — Michael M Bernshteyn
(74) *Attorney, Agent, or Firm* — Crowell & Moring LLP

(57) ABSTRACT

Provided is a water-based plaster in which the gel strength is maintained to an appropriate level in a step of producing the water-based plaster, and particularly in a spreading step and an aging step, and a final preparation can exhibit an optimal adhesiveness for adhering to the skin. In the water-based plaster, a water-based adhesive base containing a water-soluble polymer as a main ingredient contains a higher fatty acid which is a liquid at room temperature and a viscosity of 1,000 (mPa·s, 20° C.) or more as a crosslinking modifier. The higher fatty acid is isostearic acid, and the contained amount thereof is 1 to 10% by weight.

7 Claims, No Drawings

WATER-BASED PLASTER

TECHNICAL FIELD

The present invention relates to a water-based plaster, and in particular, a water-based plaster in which a water-based adhesive base containing a water-soluble polymer and a crosslinking agent as a main ingredient contains a higher fatty acid which is a liquid at room temperature and has a specific viscosity as a crosslinking modifier.

BACKGROUND ART

A water-based plaster obtained by spreading a water-based adhesive base containing a water-soluble polymer, a humectant, and water on a support such as a non-woven fabric has been widely distributed in the market as a pharmaceutical preparation for anti-inflammatory and analgesia or a refrigerant.

A method for adjusting the gel strength of a water-based adhesive base by crosslinking carboxyl groups in a polycarboxylic acid and a salt thereof which are water-soluble polymers with aluminum ions generated by dissolving an aluminum compound which is one of base ingredients to be contained in the water-based adhesive base has been often used. The degree of crosslinking is a factor of influencing the adhesiveness of a water-based plaster as a final preparation, and in addition, a factor of significantly influencing the workability in a production process.

The process of producing a water-based plaster is broadly divided into steps of mixing respective base ingredients (kneading step), thinly spreading (coating) the mixed base ingredients on a non-woven fabric or the like (spreading step), cutting a preparation obtained in the spreading step into a desired size (cutting step), and aging the cut preparation, that is, allowing the preparation to stand and storing the preparation until the gel strength is in a steady state by the development of crosslinking reaction between a water-soluble polymer and a crosslinking agent (aging step).

However, when the crosslinking rate of the water-based adhesive base in the water-based plaster is not sufficiently adjusted, the viscosity of a mixture may rapidly increase in the kneading step. Further, in the spreading step, the mixed base ingredients cannot be uniformly spread on the support, to cause spread unevenness (a state where a paste is non-uniformly spread).

In addition, when a support having a high air permeability such as a non-woven fabric is used, a paste permeates the non-woven fabric and exudes from the back side in the aging step. Thus, an undesirable influence in terms of quality may occur.

Therefore, it is very important in the production of the water-based plaster that the degree of crosslinking of the water-based adhesive base is closely adjusted. Various attempts have been conventionally made.

Patent Document 1 discloses a poutic mainly containing an aluminum salt of water-soluble polymer of an aliphatic carboxylic acid such as polyacrylic acid or a salt thereof. Patent Document 1 describes that the reaction rate of the polymer depends on the dissolution rate of a water-insoluble aluminum compound, that is, the surface area and the solubility product of the water-insoluble aluminum compound and the pH of a solution, and that a crosslinking reaction can be controlled by addition of an organic acid having an OH group in the molecule or a salt thereof.

Similarly, Patent Document 2 focuses on a combination of polyacrylic acid and a salt thereof which are water-soluble polymers forming a skeleton of hydrous gel. Patent Document 2 has proposed a hydrous gel plaster base which has a high gel strength from immediately after production, that is, a good processability, by using a monovalent salt of macromolecular polyacrylic acid and a low molecular polyacrylic acid in combination, and a highly water-soluble aluminum salt as a crosslinking agent.

Patent Document 3 discloses a method for producing a hydrous paste, in which in a step of mixing base ingredients, a polyvalent metal salt, a macromolecular compound, water, and the like are mixed in advance under a condition of low pH, and the pH of the paste is then increased during mixing other base ingredients.

However, in the water-based plaster disclosed in Patent Document 1, the gel strength significantly depends on the physicochemical properties of the water-insoluble aluminum compound to be contained. Therefore, a very severe quality control is needed. In addition, the fine mixing adjustment of the base ingredients is required. This is because the crosslinking is not promoted by an excessively large amount of organic acid (oxyacid) having an OH group.

In Patent Document 2, when the highly water-soluble aluminum salt is used as the crosslinking agent, aluminum ions are dissolved from immediately after production. For this reason, as the gel strength is higher and the spreading time is longer, gelation is promoted to remarkably increase the viscosity of the resulting water-based adhesive base. Therefore, Patent Document 2 has a problem in which a time of spreading a paste on a support is limited to a short period of time.

In Patent Document 3, when the viscosity of the hydrous paste is excessively increased in a spreading step, the paste may be non-uniformly spread on the support.

PRIOR ART DOCUMENTS

Patent Documents

Patent Document 1: JP Sho60-226808 A
Patent Document 2: JP Sho62-63512 A
Patent Document 3: JP 2001-122771 A

SUMMARY OF THE INVENTION

Problems to be Solved by the Invention

Thus, it is an object of the present invention to provide a water-based plaster in which the gel strength is maintained to an appropriate level in a step of producing the water-based plaster, and particularly in a spreading step and an aging step, and a final preparation can exhibit an optimal adhesiveness for adhering to the skin.

The present inventors have intensively studied to achieve the object. As a result, the inventors have found that surprisingly, when a water-based adhesive base contains a higher fatty acid which is a liquid at room temperature and has a viscosity of 1,000 (mPa·s, 20° C.) or more as a crosslinking modifier, a water-based plaster in which spread unevenness or the like is not caused in a spreading step, the exudation of a paste from the back side of a non-woven fabric is not observed in an aging step, and the adhesiveness is excellent is obtained. The present invention has thus been completed.

Here, "mPa·s" is referred to as "millipascal-second," and is a unit of viscosity in the international system of units.

Means for Solving the Problem

A basic aspect of the present invention is a water-based plaster in which a water-based adhesive base containing a water-soluble polymer and a crosslinking agent as main ingredients contains a higher fatty acid which is a liquid at room temperature and has a viscosity of 1,000 (mPa·s, 20° C.) or more as a crosslinking modifier.

Specifically, in the water-based plaster of the present invention, the higher fatty acid is isostearic acid.

More specifically, in the water-based plaster of the present invention, the contained amount of the higher fatty acid is 1 to 10% by weight.

Further, in the water-based plaster of the present invention, the water-soluble polymer contained is one or two or more kinds of polyacrylic acid, polyvinyl alcohol, and hydroxypropyl cellulose.

Specifically, in the water-based plaster of the present invention, the crosslinking agent is an aluminum compound.

Effects of the Invention

According to the present invention, when the water-based adhesive base containing a water-soluble polymer and a crosslinking agent as main ingredients contains a higher fatty acid which is a liquid at room temperature and has a viscosity of 1,000 (mPa·s, 20° C.) or more, a water-based plaster in which spread unevenness or the like of a paste is not caused in a spreading step, the exudation of the paste from the back side of a non-woven fabric is not observed in an aging step, and the adhesiveness is excellent can be provided.

Specifically, the water-based plaster provided by the present invention uses a higher fatty acid which is a liquid at room temperature and has a specific viscosity as a crosslinking modifier. As a result, the occurrence of spread unevenness of a paste and the exudation of the paste from the back side of the non-woven fabric in the aging step, which is observed in the conventional step of producing a water-based plaster, is not recognized in the water-based plaster. The water-based plaster is highly specific.

EMBODIMENTS FOR CARRYING OUT THE INVENTION

In the water-based plaster provided by the present invention, it is preferable that a higher fatty acid which is a liquid at room temperature and has a viscosity of 1,000 (mPa·s, 20° C.) or more be used as a crosslinking modifier contained in a water-based adhesive base containing a water-soluble polymer and a crosslinking agent as main ingredients.

When the viscosity of the higher fatty acid is less than 1,000 (mPa·s, 20° C.), crosslinking cannot be controlled. As a result, spread unevenness may be caused in the spreading step. In particular, when a paste is spread on a non-woven fabric as a support, the paste may exude from the non-woven fabric side. Therefore, this is not preferable.

Examples of such a higher fatty acid may include linolenic acid, linoleic acid, oleic acid, and isostearic acid. In particular, isostearic acid is preferably used.

The contained amount of the higher fatty acid as the crosslinking modifier in a paste composition is 1 to 10% by weight, and preferably 2 to 8% by weight.

When the contained amount of the higher fatty acid is less than 1% by weight, crosslinking between a carboxyl group and an aluminum ion in the water-based adhesive base cannot be controlled by the higher fatty acid. Therefore, the paste cannot be uniformly spread on a support.

In contrast, when the contained amount is more than 10% by weight, the compatibility with other base ingredients deteriorates, and the higher fatty acid may exude from the surface of the paste or the non-woven fabric side. This is a cause of a decrease in the adhesive power of the water-based plaster, or a cause of tackiness.

Examples of the water-soluble polymer used as the main ingredient of the water-based adhesive base in the water-based plaster provided by the present invention may include gelatin, hydrolyzed gelatin, polyacrylic acid, sodium polyacrylate, partially neutralized polyacrylic acid, polyacrylic acid starch, polyvinyl alcohol, polyvinyl pyrrolidone, hydroxypropylcellulose, hydroxypropylmethylcellulose, hydroxyethylcellulose, methylcellulose, carmellose sodium, carboxyvinyl polymer, a methoxy ethylene-maleic anhydride copolymer, a methyl acrylate-2-ethylhexyl acrylate copolymer resin emulsion, xanthan gum, and gum arabic.

In the present invention, a comparatively large amount of higher fatty acid is contained. Therefore, among water-soluble polymers, a water-soluble polymer exhibiting an effect of emulsifier is preferably used.

Examples of such a water-soluble polymer may include polyacrylic acid, polyvinyl alcohol, polyvinyl pyrrolidone, hydroxypropylcellulose, hydroxypropylmethyl cellulose, hydroxyethylcellulose, methylcellulose, and carmellose sodium, and particularly one or a combination of two or more kinds of polyacrylic acid, polyvinyl alcohol, and hydroxypropylcellulose is preferably used.

The contained amount of the water-soluble polymer in the paste composition is 3 to 20% by weight, and preferably 5 to 15% by weight.

When the contained amount is less than 3% by weight, the paste viscosity is too low. Therefore, it is difficult that the paste composition is shaped into a plaster. In contrast, when the contained amount is more than 20% by weight, the water-soluble polymer is not dissolved uniformly in the paste, and the paste is not uniform. Therefore, this is not preferable.

The contained amount of water is 30 to 60% by weight, and preferably 35 to 50% by weight, relative to the weight of the paste.

When the water content is more than 60% by weight, the paste viscosity decreases, and as a result, the shape retention ability deteriorates and the paste becomes tacky. Further, the adhesive strength significantly decreases and a sufficient sticky power on a site to which the plaster is applied is not obtained. Therefore, this is not preferable.

In contrast, when the water content is less than 30% by weight, the paste viscosity excessively increases, and the workability in the spreading step deteriorates. Further, the adhesive power increases excessively, and therefore skin stimulation such as pain during peeling of the plaster occurs. Such a water content is not preferable.

In the water-based plaster provided by the present invention, examples of the crosslinking agent used may include a water-insoluble aluminum compound such as dried aluminum hydroxide gel, synthetic aluminum silicate, dihydroxy aluminum aminoacetate, synthetic hydrotalcite, magnesium aluminometasilicate, and magnesium aluminosilicate, and a highly water-soluble aluminum salt such as potassium alum, ammonium alum, aluminum sulfate, aluminum chloride, and aluminum acetate. They may be used singly or in combination of two or more thereof.

The contained amount thereof varies depending on the kind, and is preferably 0.01 to 1% by weight.

In the water-based plaster provided by the present invention, the water-based adhesive base contains a humectant. Examples of the humectant may include concentrated glycerin, D-sorbitol solution, 1,3-butylene glycol, dipropylene glycol, polyethylene glycol, polypropylene glycol, and a pyrrolidone carboxylic acid salt. They may be used singly or in combination of two or more thereof.

The contained amount thereof is 10 to 55% by weight, preferably 10 to 45% by weight, and more preferably 15 to 35% by weight.

The water-based plaster of the present invention can contain a medicinal ingredient. Examples of the medicinal ingredient in the water-based plaster of the present invention may include, but are not limited to, loxoprofen sodium, ketoprofen, flurbiprofen, ibuprofen, zaltoprofen, fenbufen, pranoprofen, piroxicam, meloxicam, felbinac, mefenamic acid, indomethacin, diclofenac sodium, diphenhydramine, methyl salicylate, glycol salicylate, dibucaine, procaine, oxybuprocaine, lidocaine, glycyrrhetinic acid, betamethasone valerate, hydrocortisone acetate, dexamethasone acetate, deprodone propionate, croconazole hydrochloride, lanoconazole, oxiconazole, miconazole nitrate, and isoconazole nitrate. The medicinal ingredients may be used singly or in combination of two or more kinds thereof, if necessary.

In addition, in the water-based plaster of the present invention, an excipient such as kaolin, titanium oxide, anhydrous silicic acid, zinc oxide, and bentonite, a stabilizing agent such as edetate, tartaric acid, citric acid, sodium bisulfite, and diisopropanolamine, an antioxidant such as tocopherol acetate, ascorbic acid, butylhydroxytoluene, and tocopherol, a refreshing agent such as L-menthol, mentha oil, dl-camphor, and d-borneol, a capsicum-derived substance such as capsicum power, capsicum extract, and capsicum tincture, a capsaicin analogue such as capsaicin, dihydroxycapsaicin, and capsinoid, a calefacient such as nonylic acid vanillylamide and benzyl nicotinate, a preservative such as methylparaben and propylparaben, a plasticizer such as a fatty acid ester, crotamiton, and vegetable oil, and a surfactant such as a polyglycerol fatty acid ester, polyoxyethylene alkyl ether, a sorbitan fatty acid ester, polyoxyethylene hydrogenated castor oil, a propylene glycol fatty acid ester, sorbitan monooleate, and oleyl ether can be appropriately contained in a sufficient amount, if necessary.

The method for producing the water-based plaster provided by the present invention is not particularly limited, and the water-based plaster can be produced in accordance with a conventionally known production method. For example, the water-based plaster can be formed by spreading a plaster base containing the base ingredients as described above on a support and coating the surface of the water-based base with a plastic film.

As the plastic film for coating the surface of the plaster base on the support, polyethylene, polypropylene, polyester, and poly(vinyl chloride) may be used singly or in a bonded state, and the surface of the film may be subjected to a silicone treatment, a corona discharge treatment, a roughening treatment, a plasma treatment, or the like.

Examples of the support may include a porous material, a foam, a woven fabric, and a non-woven fabric of polyethylene, polypropylene, poly(vinyl chloride), polyester, nylon, and polyurethane, and a laminate of a film or sheet with the porous material, the foam, the woven fabric, or the non-woven fabric. In particular, the non-woven fabric is preferable.

As a fiber material for the non-woven fabric, polyethylene, polyproprylene, rayon, polyester, nylon, polyamide, or polyurethane is used. Examples of the production method therefor may include a needle-punching method, a spun-lace method, a spun-bonding method, a stitch-bonding method, and a melt-blowing method. The basis weight of the non-woven fabric is not particularly limited, and preferably about 50 to about 150 $g/m^2$.

It is preferable that the non-woven fabric as the support has stretchability and the lengthwise and/or widthwise elongation ratio of the non-woven fabric be 100% or more.

EXAMPLES

Hereinafter, the present invention will be described more specifically with reference to Examples and Comparative Examples, but the present invention is not limited thereto.

Example 1

2.5 g of purified water was added to 1.1 g of loxoprofen sodium hydrate, and stirred for dissolution to prepare a main drug solution. Subsequently, 25 g of 70% D-sorbitol solution, 3 g of kaolin, 0.5 g of titanium oxide, 0.5 g of tartaric acid, 0.06 g of disodium edetate hydrate, 5.0 g of 20% polyacrylic acid aqueous solution, 2.5 g of 33% polyvinyl alcohol aqueous solution, 1.0 g of methyl acrylate-2-ethylhexyl acrylate copolymer resin emulsion, and the remainder (a sufficient amount) of purified water were successively added and mixed.

A solution in which 0.1 g of methylparaben and 0.05 g of propyl paraben were dissolved in a mixed solvent of 1.0 g of propylene glycol and 0.5 g of mentha oil was added to the solution, and homogeneously mixed. To the solution, a dispersion solution in which 4.0 g of carmellose sodium, 5.0 g of sodium polyacrylate, 0.25 g of hydroxypropylcellulose, and 0.09 g of dihydroxyaluminum aminoacetate were dispersed in 20 g of concentrated glycerin was added, and the mixture was homogeneously mixed. Finally, the main drug solution and 3.0 g of isostearic acid were added and mixed to obtain a water-based adhesive base. This water-based adhesive base was spread on a polyester non-woven fabric, and the surface of the adhesive base was coated with a plastic film to form a water-based plaster.

Examples 2 to 7

A water-based plaster of each Example was produced in the same manner as in Example 1 except that formulations (unit: % by weight) shown in Table 1 were used.

The formulation of Example 1 is also shown in Table 1.

TABLE 1

| Ingredients | Examples | | | | | | |
| --- | --- | --- | --- | --- | --- | --- | --- |
| | 1 | 2 | 3 | 4 | 5 | 6 | 7 |
| Mentha oil | 0.5 | 0.5 | 0.5 | 0.5 | — | 0.5 | 0.5 |
| Propylene glycol | 1.0 | 1.0 | 1.0 | 1.0 | 3.0 | 1.0 | 1.0 |
| Methyl acrylate-2-ethyl-hexyl acrylate copolymer resin emulsion | 1.0 | 1.0 | 1.0 | 1.0 | 1.0 | 1.0 | 1.0 |
| Loxoprofen hydrate | 1.1 | 1.1 | 1.1 | 1.1 | 1.1 | — | — |

TABLE 1-continued

| Ingredients | 1 | 2 | 3 | 4 | 5 | 6 | 7 |
|---|---|---|---|---|---|---|---|
| Flurbiprofen | — | — | — | — | — | 0.5 | — |
| Isostearic acid | 3.0 | 3.0 | 3.0 | 10.0 | 3.0 | 3.0 | 3.0 |
| Kaolin | 3.0 | 3.0 | 3.0 | 3.0 | 3.0 | 3.0 | 3.0 |
| Titanium oxide | 0.5 | 0.5 | 0.5 | 0.5 | — | 0.5 | 0.5 |
| 33% Polyvinyl alcohol aqueous solution | 2.5 | 2.5 | 2.5 | 2.5 | — | 2.5 | 2.5 |
| Hydroxypropylcellulose | 0.25 | 0.25 | 0.25 | 0.25 | 0.25 | 0.25 | 0.25 |
| D-Sorbitol solution | 25 | 25 | 25 | 18 | 14 | 25 | 25 |
| Concentrated glycerin | 25 | 25 | 25 | 25 | 35 | 25 | 25 |
| Carmellose sodium | 4.0 | 4.0 | 4.0 | 4.0 | 4.0 | 4.0 | 4.0 |
| Sodium polyacrylate | 5.0 | 5.0 | 5.0 | 5.0 | 5.0 | 5.0 | 5.0 |
| 20% Polyacrylic acid aqueous solution | 5.0 | 5.0 | 5.0 | 5.0 | 4.0 | 5.0 | 5.0 |
| Tartaric acid | 0.5 | 0.5 | 0.5 | 0.5 | 0.5 | 0.5 | 0.5 |
| Methyl paraben | 0.1 | 0.1 | 0.1 | 0.1 | 0.1 | 0.1 | 0.1 |
| Dihydroxy aluminum aminoacetate | 0.09 | — | 0.09 | 0.09 | 0.33 | 0.09 | 0.09 |
| Potassium alum | — | 0.2 | — | — | — | — | — |
| Propyl paraben | 0.05 | 0.05 | 0.05 | 0.05 | 0.05 | 0.05 | 0.05 |
| Disodium edetate hydrate | 0.06 | 0.06 | 0.06 | 0.06 | 0.12 | 0.06 | 0.06 |
| Purified water | q.s. | q.s. | q.s. | q.s. | q.s. | q.s. | q.s. |
| Support | | | Polyester non-woven fabric | | | | |
| Basis weight (g/cm$^2$) | 90 | 110 | 90 | 110 | 90 | 90 | 90 |
| Viscosity of Isostearic acid | 5400 | 6000 | 1000 | 6000 | 3400 | 5400 | 5400 |

Unit: (mPa/s, 20° C.)

Comparative Examples 1 to 5

Water-based plasters of Comparative Examples 1 to 5 were produced in the same manner as in Example 1 except that formulations (unit: % by weight) shown in Table 2 were used.

TABLE 2

| Ingredients | 1 | 2 | 3 | 4 | 5 |
|---|---|---|---|---|---|
| Mentha oil | 0.5 | 0.5 | 0.5 | 0.5 | 0.5 |
| Propylene glycol | 1.0 | 1.0 | 1.0 | 1.0 | 1.0 |
| Methyl acrylate-2-ethyl-hexyl acrylate copolymer resin emulsion | 1.0 | 1.0 | 1.0 | 1.0 | 1.0 |
| Loxoprofen hydrate | 1.1 | 1.1 | 1.1 | — | 1.1 |
| Isostearic acid | 3.0 | 3.0 | — | 3.0 | 15.0 |
| Kaolin | 3.0 | 3.0 | 3.0 | 3.0 | 3.0 |
| Titanium oxide | 0.5 | 0.5 | 0.5 | 0.5 | 0.5 |
| 33% Polyvinyl alcohol aqueous solution | 2.5 | 2.5 | 2.5 | 2.5 | 2.5 |
| Hydroxypropylcellulose | 0.25 | 0.25 | 0.25 | 0.25 | 0.25 |
| D-Sorbitol solution | 25 | 25 | 18 | 25 | 12 |
| Concentrated glycerin | 25 | 25 | 25 | 25 | 25 |
| Carmellose sodium | 4.0 | 4.0 | 4.0 | 4.0 | 4.0 |
| Sodium polyacrylate | 5.0 | 5.0 | 5.0 | 5.0 | 5.0 |
| 20% Polyacrylic acid aqueous solution | 5.0 | 5.0 | 5.0 | 5.0 | 5.0 |
| Tartaric acid | 0.5 | 0.5 | 0.5 | 0.5 | 0.5 |
| Methyl paraben | 0.1 | 0.1 | 0.1 | 0.1 | 0.1 |
| Dihydroxy aluminum aminoacetate | 0.09 | — | — | 0.09 | 0.09 |
| Potassium alum | — | 0.2 | 0.2 | — | — |
| Propyl paraben | 0.05 | 0.05 | 0.05 | 0.05 | 0.05 |
| Disodium edetate hydrate | 0.06 | 0.06 | 0.06 | 0.06 | 0.06 |
| Purified water | q.s. | q.s. | q.s. | q.s. | q.s. |
| Support | | Polyester non-woven fabric | | | |
| Basis weight (g/cm$^2$) | 90 | 90 | 110 | 90 | 110 |
| Viscosity of Isostearic acid | 140 | 400 | — | 140 | 5400 |

Unit: (mPa/s, 20° C.)

Test Example 1

Evaluation of Spreading State of Paste in Spreading Step

For the water-based adhesive bases in Examples 1 to 7 and Comparative Examples 1 to 5, whether a paste can be uniformly spread on a non-woven fabric having stretchability immediately after to 120 minutes after kneading was investigated.

The results are shown in Table 3.

Symbols in Tables are results based on the following evaluation criteria.

Circle (○): a paste was hardly changed by crosslinking immediately after to 120 minutes after kneading, and the paste could be uniformly spread.

Cross (X): the physical properties of a paste immediately after kneading were such that the paste could not be spread already, or the physical properties of a paste immediately after kneading were favorable, but the crosslinking rapidly proceeded and the paste could not be uniformly spread.

TABLE 3

| | Examples | | | | | | | Comparative Examples | | | | |
|---|---|---|---|---|---|---|---|---|---|---|---|---|
| | 1 | 2 | 3 | 4 | 5 | 6 | 7 | 1 | 2 | 3 | 4 | 5 |
| Evaluation | ○ | ○ | ○ | ○ | ○ | ○ | ○ | ○ | ○ | X | X | ○ |

Test Example 2

Study of Presence or Absence of Exudation of Paste from Non-woven Fabric in Aging Step A load of about 2 kg was applied to the water-based plaster of each of Examples 1 to 4, and 6, and Comparative Examples 1 to 3, and 5, and the water-based plaster was stored for 7 days under storage conditions of 20° C. and 40° C. The presence or absence of exudation of the sample from the back side of the non-woven fabric was visually observed and evaluated.

The results are shown in Table 4. The results are shown based on the following evaluation criteria.

Evaluation Criteria

Circle (○): the exudation of a paste component was not observed on the back side of the non-woven fabric.

Triangle (Δ): the exudation of a paste component was slightly observed on the back side of the non-woven fabric.

Cross (X): the exudation of a paste component was remarkably observed on the back side of the non-woven fabric.

TABLE 4

| Storage temperature | Examples | | | | | Com. Examples | | | |
|---|---|---|---|---|---|---|---|---|---|
| | 1 | 2 | 3 | 4 | 6 | 1 | 2 | 3 | 5 |
| 20° C. | ○ | ○ | ○ | ○ | ○ | X | ○ | ○ | X |
| 40° C. | ○ | ○ | ○ | ○ | ○ | X | X | Δ | X |

Test Example 3

Patch Test

The water-based plaster of each of Examples 1 to 4, and 6, and Comparative Examples 1 to 3 was aged at room temperature for 30 days. After informed consent was obtained, each preparation (10 cm×7 cm) was attached to the forearm of each of four subjects for 8 hours. The attachment state was evaluated. The state of the preparation 8 hours after the initiation of attachment was evaluated in accordance with the following evaluation criteria, and the result of the patch test was represented by the average of the four subjects.

The results are shown in Table 5.

Evaluation Criteria

4: a plaster was not peeled.
3: a plaster was partly peeled.
2: more than half of a plaster was peeled.
1: a plaster fell in the test.

TABLE 5

| | Examples | | | | | Com. Examples | | |
|---|---|---|---|---|---|---|---|---|
| Patch Test | 1 | 2 | 3 | 4 | 6 | 1 | 2 | 3 |
| Average | 3.5 | 4.0 | 4.0 | 3.8 | 3.5 | 2.5 | 1.0 | 1.8 |

SPECIFIC EXAMPLES OF PREPARATIONS

Hereinafter, specific examples of preparations other than the water-based plaster of the present invention shown in Table 1 are shown in Table 6 (unit: % by weight). Here, the present invention is not limited to the example.

TABLE 6

| Ingredients | Examples of Preparations | | | |
|---|---|---|---|---|
| | 1 | 2 | 3 | 4 |
| Mentha oil | 0.5 | — | 0.5 | 0.5 |
| Propylene glycol | 3.0 | 3.0 | 1.0 | 5.0 |
| Methyl acrylate-2-ethyl-hexyl acrylate copolymer resin emulsion | 1.0 | 1.0 | 1.0 | 1.0 |

TABLE 6-continued

| Ingredients | Examples of Preparations | | | |
|---|---|---|---|---|
| | 1 | 2 | 3 | 4 |
| Loxoprofen hydrate | — | — | 1.1 | — |
| Flurbiprofen | 0.5 | — | — | — |
| Diclofenac sodium | — | 1 | — | — |
| Lidocaine | — | — | — | 2 |
| Isostearic acid | 5.0 | 5.0 | 7.0 | 10.0 |
| Kaolin | 3.0 | 3.0 | 3.0 | 3.0 |
| Titanium oxide | 0.5 | — | 0.5 | 0.5 |
| 33% Polyvinyl alcohol aqueous solution | 2.5 | — | 2.5 | 2.5 |
| Hydroxypropylcellulose | 0.25 | 0.25 | 0.25 | 0.25 |
| D-Sorbitol solution | 25 | 20 | 20 | 20 |
| Concentrated glycerin | 20 | 25 | 20 | 20 |
| Carmellose sodium | 4.0 | 4.0 | 4.0 | 4.0 |
| Sodium polyacrylate | 5.0 | 5.0 | 5.0 | 5.0 |
| 20% Polyacrylic acid aqueous solution | 5.0 | 4.0 | 5.0 | 5.0 |
| Tartaric acid | 0.5 | 0.5 | 0.5 | 0.5 |
| Methyl paraben | 0.1 | 0.1 | 0.1 | 0.1 |
| Dihydroxy aluminum aminoacetate | 0.09 | 0.33 | 0.09 | 0.12 |
| Propyl paraben | 0.05 | 0.05 | — | — |
| Disodium edetate hydrate | 0.06 | 0.12 | 0.06 | 0.06 |
| Purified water | q.s. | q.s. | q.s. | q.s. |
| Support | Polyester non-woven fabric | | | |
| Basis weight (g/cm$^2$) | 110 | 110 | 110 | 110 |
| Viscosity of Isostearic acid | 5400 | 3400 | 6000 | 6000 |

Unit: (mPa/s, 20° C.)

In the water-based plasters of Comparative Examples, the paste was not uniformly spread for 120 minutes after kneading (Comparative Examples 3 and 4), and the exudation of the paste from the back side of the non-woven fabric in the aging step was observed (Comparative Examples 1 to 3, and 5). From the above-described results, it is clear that crosslinking of the paste is not sufficiently controlled. Since the crosslinking is not sufficiently controlled, the adhesive power of the final preparation of each Comparative Example is insufficient.

On the other hand, in the water-based plaster of the present invention, the workability in the spreading step is excellent. The exudation of the paste from the back side of the support is not observed in the aging step. Further, the final preparation exhibits good adhesiveness. Thus, the crosslinking of the paste is well controlled by the formulation of a higher fatty acid which is a liquid at room temperature and has a viscosity of 1,000 (mPa·s, 20° C.) or more. Therefore, it is demonstrated that the water-based plaster is suitable for the workability during production and the adhesiveness of the final preparation.

INDUSTRIAL APPLICABILITY

As described above, when a water-based adhesive base containing a water-soluble polymer as a main ingredient contains a higher fatty acid which is a liquid at normal temperature and has a viscosity of 1,000 (mPa·s, 20° C.) or more as a crosslinking modifier, the present invention can provide a water-based plaster in which spread unevenness or the like of a paste is not caused in a spreading step, the exudation of a paste from the back side of a non-woven fabric is not observed in an aging step, and the adhesiveness is excellent. In this respect, the water-based plaster has high industrial applicability.

The invention claimed is:

1. A water-based plaster comprising a water-based adhesive base containing a water-soluble polymer and a crosslinking agent as main ingredients and a higher fatty acid which is a liquid at room temperature and has a viscosity of 1,000 (mPa·s, 20° C.) or more as a crosslinking modifier, wherein the higher fatty acid is in an amount of 1-10% by weight of the plaster.

2. The water-based plaster according to claim 1, wherein the higher fatty acid is isostearic acid.

3. The water-based plaster according to claim 1, wherein the water-soluble polymer contained is one or two or more kinds of polyacrylic acid, polyvinyl alcohol, and hydroxypropyl-cellulose.

4. The water-based plaster according to claim 1, wherein the crosslinking agent is an aluminum compound.

5. The water-based plaster according to claim 2, wherein the water-soluble polymer contained is one or two or more kinds of polyacrylic acid, polyvinyl alcohol, and hydroxypropyl-cellulose.

6. The water-based plaster according to claim 2, wherein the crosslinking agent is an aluminum compound.

7. A water-based plaster comprising a water-based adhesive base containing a water-soluble polymer and a crosslinking agent as main ingredients and an isostearic acid which is liquid at room temperature and has a viscosity of 1,000 (mPa·s, 20° C.), or more, as a crosslinking modifier, wherein the isostearic acid is in an amount of 1-10% by weight of the plaster, the water-soluble polymer is one or two or more kinds of polyacrylic acid, polyvinyl alcohol, and hydroxypropyl-cellulose, and present in an amount of 3% to 20% by weight of the plaster, and wherein the crosslinking agent is an aluminum compound in an amount of 0.01-1% by weight of the plaster.

\* \* \* \* \*